United States Patent
Stone et al.

(10) Patent No.: US 8,900,301 B2
(45) Date of Patent: Dec. 2, 2014

(54) METHOD AND APPARATUS FOR GRAFT FIXATION

(75) Inventors: Kevin T. Stone, Winona Lake, IN (US); Jason D. Meridew, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 31 days.

(21) Appl. No.: 13/419,681

(22) Filed: Mar. 14, 2012

(65) Prior Publication Data

US 2012/0172986 A1 Jul. 5, 2012

Related U.S. Application Data

(63) Continuation of application No. 11/717,792, filed on Mar. 13, 2007, now Pat. No. 8,147,546.

(51) Int. Cl.
*A61F 2/08* (2006.01)
*A61B 17/86* (2006.01)

(52) U.S. Cl.
CPC .............. *A61F 2/08* (2013.01); *A61B 17/8645* (2013.01); *A61F 2/0811* (2013.01); *A61F 2002/0829* (2013.01); *A61F 2002/0858* (2013.01); *A61F 2002/0864* (2013.01); *A61F 2002/087* (2013.01); *A61F 2002/0882* (2013.01)
USPC ................... 623/13.14; 623/13.11; 623/13.17

(58) Field of Classification Search
USPC ........... 623/13.11–13.12, 13.14–13.15, 13.17
See application file for complete search history.

(56) References Cited

U.S. PATENT DOCUMENTS

| | | | |
|---|---|---|---|
| 461,621 | A | 10/1891 | Rogers |
| 1,762,394 | A | 6/1930 | Hosking |
| 1,940,878 | A | 12/1933 | Olson |
| 2,640,521 | A | 6/1953 | Zavoico |
| 2,695,607 | A | 11/1954 | Hipps et al. |
| 3,832,931 | A | 9/1974 | Talan |
| 3,871,379 | A | 3/1975 | Clarke |
| 4,044,647 | A | 8/1977 | Takahashi et al. |
| 4,053,982 | A | 10/1977 | Weissman |
| D249,705 | S | 9/1978 | London |
| 4,257,411 | A | 3/1981 | Cho |
| 4,338,054 | A | 7/1982 | Dahl |
| 4,386,179 | A | 5/1983 | Sterling |

(Continued)

FOREIGN PATENT DOCUMENTS

| | | |
|---|---|---|
| EP | 1360949 | 11/2003 |
| FR | 2684543 A1 | 6/1993 |

OTHER PUBLICATIONS

Allen et al., "Degradation and stabilization of styrene-ethylene-butadiene-styrene (SEBS) block copolymer", Polymer Degradation and Stability, V. 71, p. 113-122. (2001).

*Primary Examiner* — David H Willse
*Assistant Examiner* — Tiffany Shipmon
(74) *Attorney, Agent, or Firm* — Harness, Dickey

(57) ABSTRACT

A device for surgically coupling a soft tissue graft into a tunnel of a bone. The device includes a first member and a second member. The first member includes a first graft-engaging surface extending from a first end to a second end of the first member. The second member includes a second graft-engaging surface extending from a first end to a second end of the second member. The first graft-engaging surface and the second graft-engaging surface define a graft-accepting through-passage with a longitudinal axis extending therethrough when the first member is secured to the second member.

27 Claims, 5 Drawing Sheets

(56) References Cited

U.S. PATENT DOCUMENTS

| | | |
|---|---|---|
| 4,535,768 A | 8/1985 | Hourahane et al. |
| 4,537,185 A | 8/1985 | Stednitz |
| 4,756,307 A | 7/1988 | Crowninshield |
| 4,903,692 A | 2/1990 | Reese |
| 4,922,897 A | 5/1990 | Sapega et al. |
| 4,932,972 A | 6/1990 | Dunn et al. |
| 4,950,270 A | 8/1990 | Bowman et al. |
| 4,985,032 A | 1/1991 | Goble |
| 4,998,937 A | 3/1991 | Grimes |
| 5,004,474 A | 4/1991 | Fronk et al. |
| 5,019,078 A | 5/1991 | Perren et al. |
| 5,026,374 A | 6/1991 | Dezza et al. |
| 5,030,219 A | 7/1991 | Matsen, III et al. |
| 5,041,129 A | 8/1991 | Hayhurst et al. |
| 5,098,435 A | 3/1992 | Stednitz et al. |
| 5,100,405 A | 3/1992 | McLaren |
| 5,100,417 A | 3/1992 | Cerier et al. |
| 5,108,396 A | 4/1992 | Lackey et al. |
| 5,112,336 A | 5/1992 | Krevolin et al. |
| 5,129,902 A | 7/1992 | Goble et al. |
| 5,139,520 A | 8/1992 | Rosenberg |
| 5,141,520 A | 8/1992 | Goble et al. |
| 5,176,682 A | 1/1993 | Chow |
| 5,192,322 A | 3/1993 | Koch et al. |
| 5,201,744 A | 4/1993 | Jones |
| 5,224,946 A | 7/1993 | Hayhurst et al. |
| 5,234,434 A | 8/1993 | Goble et al. |
| 5,234,444 A | 8/1993 | Christoudias |
| 5,257,996 A | 11/1993 | McGuire |
| 5,258,016 A | 11/1993 | DiPoto et al. |
| 5,266,075 A | 11/1993 | Clark et al. |
| 5,300,077 A | 4/1994 | Howell |
| 5,350,380 A | 9/1994 | Goble et al. |
| 5,354,298 A | 10/1994 | Lee et al. |
| 5,354,300 A | 10/1994 | Goble et al. |
| 5,356,413 A | 10/1994 | Martins et al. |
| 5,370,646 A | 12/1994 | Reese et al. |
| 5,370,662 A | 12/1994 | Stone et al. |
| 5,391,029 A | 2/1995 | Fardell |
| 5,393,302 A | 2/1995 | Clark et al. |
| 5,397,356 A | 3/1995 | Goble et al. |
| D357,534 S | 4/1995 | Hayes |
| 5,423,823 A | 6/1995 | Schmieding |
| 5,425,733 A | 6/1995 | Schmieding |
| 5,431,651 A | 7/1995 | Goble |
| 5,437,677 A | 8/1995 | Shearer et al. |
| 5,454,365 A | 10/1995 | Bonutti |
| 5,456,722 A | 10/1995 | McLeod et al. |
| 5,480,403 A | 1/1996 | Lee et al. |
| 5,507,812 A | 4/1996 | Moore |
| 5,540,703 A | 7/1996 | Barker, Jr. et al. |
| 5,545,180 A | 8/1996 | Le et al. |
| 5,549,676 A | 8/1996 | Johnson |
| 5,562,671 A | 10/1996 | Goble et al. |
| 5,593,408 A | 1/1997 | Gayet et al. |
| 5,601,562 A | 2/1997 | Wolf et al. |
| 5,618,314 A | 4/1997 | Harwin et al. |
| 5,632,748 A | 5/1997 | Beck, Jr. et al. |
| 5,643,273 A | 7/1997 | Clark |
| 5,643,320 A | 7/1997 | Lower et al. |
| 5,665,121 A | 9/1997 | Gie et al. |
| 5,674,224 A | 10/1997 | Howell et al. |
| 5,800,544 A | 9/1998 | Demopulos et al. |
| 5,849,013 A | 12/1998 | Whittaker et al. |
| 5,868,789 A | 2/1999 | Huebner |
| 5,891,150 A | 4/1999 | Chan |
| 5,895,425 A | 4/1999 | Grafton et al. |
| 5,918,604 A | 7/1999 | Whelan |
| 5,931,839 A | 8/1999 | Medoff |
| 5,931,869 A | 8/1999 | Boucher et al. |
| 5,941,885 A | 8/1999 | Jackson |
| 5,964,764 A | 10/1999 | West, Jr. et al. |
| 5,980,558 A | 11/1999 | Wiley |
| 5,984,966 A | 11/1999 | Kiema et al. |
| 6,039,739 A | 3/2000 | Simon et al. |
| 6,066,173 A | 5/2000 | McKernan et al. |
| 6,068,648 A | 5/2000 | Cole et al. |
| 6,106,556 A * | 8/2000 | Demopulos et al. ........ 623/13.16 |
| 6,110,211 A | 8/2000 | Weiss |
| 6,113,604 A | 9/2000 | Whittaker et al. |
| 6,132,433 A | 10/2000 | Whelan |
| 6,146,406 A | 11/2000 | Shluzas et al. |
| 6,187,742 B1 | 2/2001 | Wozney et al. |
| 6,224,598 B1 | 5/2001 | Jackson |
| 6,231,608 B1 | 5/2001 | Stone |
| 6,231,611 B1 | 5/2001 | Mosseri |
| 6,267,766 B1 | 7/2001 | Burkhart |
| 6,280,472 B1 | 8/2001 | Boucher et al. |
| 6,280,474 B1 | 8/2001 | Cassidy et al. |
| 6,306,138 B1 | 10/2001 | Clark et al. |
| 6,325,804 B1 | 12/2001 | Wenstrom, Jr. et al. |
| 6,342,056 B1 | 1/2002 | Mac-Thiong et al. |
| 6,371,124 B1 | 4/2002 | Whelan |
| 6,375,684 B1 | 4/2002 | Kriek et al. |
| 6,379,384 B1 | 4/2002 | McKernan et al. |
| 6,383,199 B2 | 5/2002 | Carter et al. |
| 6,436,099 B1 | 8/2002 | Drewry et al. |
| 6,440,373 B1 | 8/2002 | Gomes et al. |
| 6,454,768 B1 | 9/2002 | Jackson |
| 6,494,913 B1 | 12/2002 | Huebner |
| 6,497,726 B1 | 12/2002 | Carter et al. |
| 6,499,486 B1 | 12/2002 | Chervitz et al. |
| 6,511,958 B1 | 1/2003 | Atkinson et al. |
| 6,514,514 B1 | 2/2003 | Atkinson et al. |
| 6,517,546 B2 | 2/2003 | Whittaker et al. |
| 6,517,579 B1 | 2/2003 | Paulos et al. |
| 6,524,328 B2 | 2/2003 | Levinson |
| 6,537,319 B2 | 3/2003 | Whelan |
| 6,540,783 B1 | 4/2003 | Whittaker et al. |
| 6,558,389 B2 * | 5/2003 | Clark et al. ................. 606/916 |
| 6,562,043 B1 | 5/2003 | Chan |
| 6,562,044 B1 | 5/2003 | Cooper |
| 6,562,071 B2 | 5/2003 | Jarvinen et al. |
| 6,589,281 B2 | 7/2003 | Hyde, Jr. |
| 6,610,064 B1 | 8/2003 | Goble et al. |
| 6,623,524 B2 | 9/2003 | Schmieding |
| 6,673,115 B2 | 1/2004 | Resch et al. |
| 6,712,823 B2 | 3/2004 | Grusin et al. |
| 6,730,089 B2 | 5/2004 | Jackson |
| 6,733,529 B2 | 5/2004 | Whelan |
| 6,752,830 B1 | 6/2004 | Goble et al. |
| 6,755,840 B2 | 6/2004 | Boucher et al. |
| 6,780,188 B2 | 8/2004 | Clark et al. |
| 6,878,166 B2 | 4/2005 | Clark et al. |
| 6,887,271 B2 | 5/2005 | Justin et al. |
| 7,022,124 B2 | 4/2006 | Takei et al. |
| 7,033,364 B1 | 4/2006 | Walters et al. |
| 7,137,996 B2 * | 11/2006 | Steiner et al. .............. 623/13.14 |
| 7,229,448 B2 | 6/2007 | Goble et al. |
| 7,285,121 B2 | 10/2007 | Braun et al. |
| 7,309,337 B2 | 12/2007 | Colleran et al. |
| 7,341,592 B1 | 3/2008 | Walters et al. |
| 7,458,975 B2 | 12/2008 | May et al. |
| 7,588,595 B2 | 9/2009 | Miller et al. |
| 7,601,165 B2 | 10/2009 | Stone |
| 7,645,293 B2 | 1/2010 | Martinek et al. |
| 2001/0039455 A1 | 11/2001 | Simon et al. |
| 2001/0044627 A1 | 11/2001 | Justin |
| 2001/0047210 A1 | 11/2001 | Wolf |
| 2001/0053934 A1 | 12/2001 | Schmieding |
| 2002/0019635 A1 | 2/2002 | Wenstrom et al. |
| 2002/0058941 A1 | 5/2002 | Clark et al. |
| 2002/0077631 A1 | 6/2002 | Lubbers et al. |
| 2002/0087160 A1 | 7/2002 | Clark et al. |
| 2002/0099381 A1 | 7/2002 | Maroney |
| 2002/0111689 A1 | 8/2002 | Hyde |
| 2002/0111690 A1 | 8/2002 | Hyde |
| 2002/0133153 A1 | 9/2002 | Hyde |
| 2002/0138148 A1 | 9/2002 | Hyde |
| 2002/0138149 A1 | 9/2002 | Hyde |
| 2003/0028194 A1 | 2/2003 | St. Pierre et al. |
| 2003/0032961 A1 | 2/2003 | Pelo et al. |
| 2003/0065332 A1 | 4/2003 | TenHuisen et al. |
| 2003/0097179 A1 | 5/2003 | Carter et al. |

(56) References Cited

U.S. PATENT DOCUMENTS

| | | |
|---|---|---|
| 2003/0100903 A1* | 5/2003 | Cooper .................. 606/72 |
| 2003/0105524 A1 | 6/2003 | Paulos et al. |
| 2003/0130735 A1* | 7/2003 | Rogalski ............ 623/13.15 |
| 2003/0163202 A1 | 8/2003 | Lakin |
| 2003/0171811 A1* | 9/2003 | Steiner et al. ....... 623/13.17 |
| 2003/0191530 A1* | 10/2003 | Sklar .................. 623/13.14 |
| 2004/0087953 A1 | 5/2004 | Singhatat et al. |
| 2004/0092936 A1 | 5/2004 | Miller et al. |
| 2005/0038426 A1 | 2/2005 | Chan |
| 2005/0137704 A1 | 6/2005 | Steenlage |
| 2005/0149187 A1 | 7/2005 | Clark et al. |
| 2005/0177165 A1 | 8/2005 | Zang et al. |
| 2005/0197662 A1 | 9/2005 | Clark et al. |
| 2005/0203622 A1 | 9/2005 | Steiner et al. |
| 2005/0273003 A1 | 12/2005 | Walters et al. |
| 2006/0229722 A1 | 10/2006 | Bianchi et al. |
| 2007/0162123 A1 | 7/2007 | Whittaker et al. |
| 2007/0168043 A1 | 7/2007 | Ferree |
| 2008/0027443 A1 | 1/2008 | Lambert |
| 2008/0228271 A1 | 9/2008 | Stone et al. |
| 2011/0153018 A1 | 6/2011 | Walters et al. |

\* cited by examiner

METHOD AND APPARATUS FOR GRAFT FIXATION

CROSS-REFERENCE TO RELATED APPLICATIONS

The application is a continuation of U.S. patent application Ser. No. 11/717,792 filed on Mar. 13, 2007, the entire disclosure of which is incorporated herein by reference.

FIELD

The present disclosure relates to endoscopic soft tissue replacement fixation. More particularly, the present disclosure relates to an apparatus and a method to reconstruct an anterior cruciate ligament with soft tissue replacements within a femoral or tibial tunnel.

BACKGROUND

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

It has been difficult to insert and fasten a soft tissue replacement in a blind hole or tunnel. Attempts have been made to thread the soft tissue replacement through the tunnel and over an anchor, but with some difficulty. As such, improvements which provide a quick and efficient way to couple a soft tissue replacement to an implanted anchoring system are desirable.

Currently, fascia lata soft tissue replacements are flexible strands which are affixed to a threaded stud and turned into the femoral tunnel. Unfortunately, this procedure may result in the soft tissue replacement being wrapped upon itself during insertion. Hamstring soft tissue replacements are also currently fixed over a screw in the tibial tunnel and fixed on the lateral femur. This technique may require the femoral tunnel to completely penetrate the femur. In addition, according to present procedures, fixation of the soft tissue replacement on the femoral side may require a large incision.

Additional procedures include the use of bone-tendon-bone grafts which have been pre- or intra-operatively harvested from a donor site. In addition to the problems associated with graft retrieval, these bone-tendon-bone grafts are of fixed length. This fixed length significantly reduces their usability, as it is not possible to easily adjust the tension or length of the implanted tendon.

While offering certain improvements in arthroscopic surgery to repair ligaments, the prior art may still be improved upon to overcome the limitations of the endoscopic hamstring soft tissue replacement fixation due, in many instances, to the weakness of the mechanism used to couple the tendon soft tissue replacement to an aperture formed within a bone. Other techniques attempt to use biological fixation to augment or replace mechanical fixation. While increasing fixation strength, these techniques require time to fully realize their fixation potential. Additionally the techniques may take additional surgical time and resources that a purely mechanical fixation technique may not require.

SUMMARY

This section provides background information related to the present disclosure which is not necessarily prior art.

The present teachings provide for a device for surgically coupling a soft tissue graft into a tunnel of a bone. The device includes a first member and a second member. The first member includes a first graft-engaging surface extending from a first end to a second end of the first member. The second member includes a second graft-engaging surface extending from a first end to a second end of the second member. The first graft-engaging surface and the second graft-engaging surface define a graft-accepting through-passage with a longitudinal axis extending therethrough when the first member is secured to the second member.

The present teachings further provide for a device for surgically coupling a soft tissue graft into a tunnel of a bone. The device includes a first member and a second member. The first member includes a convex first bone-engaging surface extending from a first end to a second end of the first member, a concave first graft-engaging surface extending from the first end to the second end of the first member that is opposite to the first bone-engaging surface, and a plurality of graft-engaging members included with the first graft-engaging surface. The second member includes a convex second bone-engaging surface extending from a first end to a second end of the second member and a concave second graft-engaging surface extending from the first end to the second end of the second member that is opposite to the second bone-engaging surface. The first graft-engaging surface and the second graft-engaging surface define a graft-accepting through-passage when the first member is coupled to the second member. The graft-accepting through-passage defines a generally circular cross-section taken along a first line perpendicular to a longitudinal axis extending through the graft-accepting through-passage.

The present teachings also provide for a method for surgically coupling a soft tissue graft into a tunnel of a bone. The method includes positioning a first end of the soft tissue graft against a first graft-engaging surface of a first member, the first member including a first bone-engaging surface opposite to the first graft-engaging surface; coupling a second member to the first member to secure the first end of the soft tissue graft in a generally tubular graft-accepting passage defined by the first graft-engaging surface of the first member and a second graft-engaging surface of the second member, the coupled first member and the second member provide a first prosthetic assembly; forming the tunnel in the bone; determining an appropriate length of the soft tissue graft; inserting at least a portion of the first prosthetic assembly within the tunnel; and affixing the first prosthetic assembly in the tunnel and affixing a second end of the soft tissue graft with respect to the tunnel.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

Figure 1:
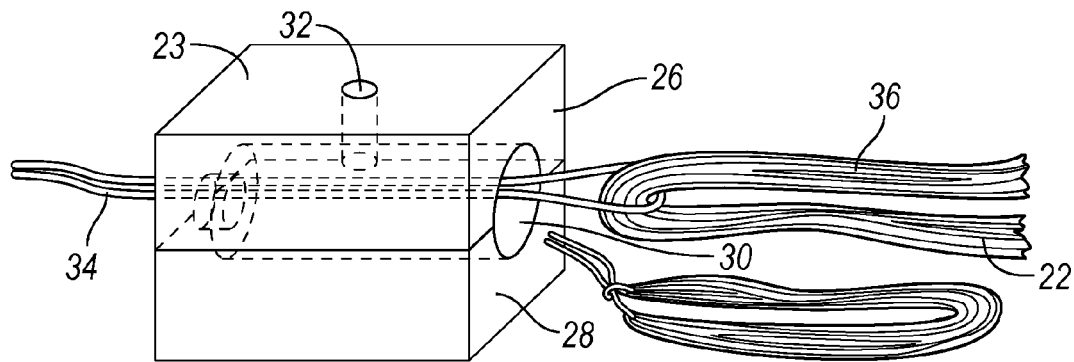
FIGS. 1 and 2 represent a method of forming a prosthetic about a graft according to one embodiment of the teachings herein.

The descriptions of the teachings are merely exemplary in nature and, thus, variations that do not depart from the gist of the teachings are intended to be within the scope of the invention. Such variations are not to be regarded as a departure from the spirit and scope of the teachings.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 2:
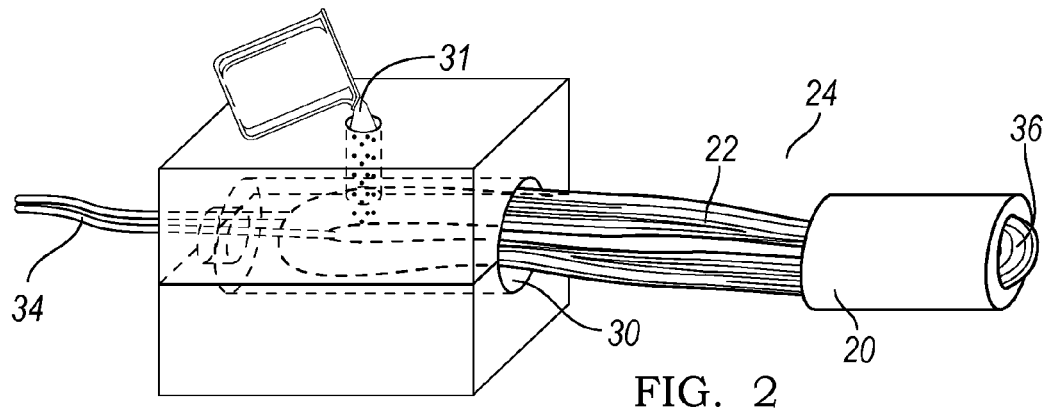

FIGS. 1 and 2 represent a system and method of forming a prosthetic 20 about a graft or graft replacement material 22 to form an artificial bone-tendon or bone-tendon-bone prosthetic assembly 24 according to one embodiment disclosed herein. Shown is a mold 23 having a first and second dies 26 and 28, which define a cavity 30 therethrough. Defined by the first die 26 is an injection port 32, which allows for the filling of the through cavity 30 with biocompatible material. As shown in FIG. 1, a suture 34 is threaded through a loop 36 of the replacement graft material 22, or tied to the ends of the graft material 22.

The suture 34 and loop 36 of graft material 22 are pulled through the through cavity 30 to position the loop 36 of graft 22 in the cavity 30. After the loop 36 of graft material 22 is placed within the through cavity 30, an uncured biocompatible polymer material 31, bone cement, or a calcium phosphate containing mixture is then injected through injection port 32. After the curing or setting of the polymer 31, the first and second dies 26 and 28 are separated exposing the prosthetic 20 intimately frictionally and/or mechanically coupled to the graft 22. In this regard, the exterior surface of a portion of the replacement graft is completely enclosed or encapsulated by the prosthetic 20. In other words, the prosthetic can function to protect this portion of the graft replacement 22 from interaction with hardware used to couple the graft assembly 24 to the bone. The replacement graft 22 may be a preoperative or intraoperatively harvested tendon such has a hamstring or may be xenograft, allograft, or artificial graft material.

Figure 3A:
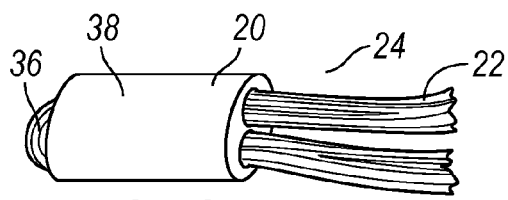
FIGS. 3a-3c represent prosthetics formed using the method shown in FIGS. 1 and 2.
Figure 3B:
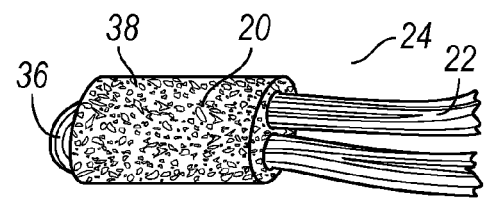
Figure 3C:
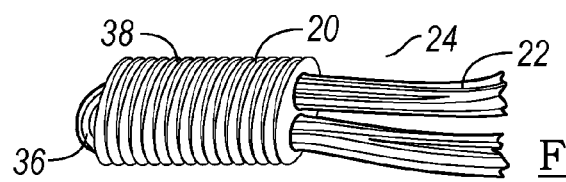

As shown in FIGS. 3a-3c, the exterior surface 38 of the prosthetic 20 can be textured by modifying the interior surface of the cavity 30. In this regard, the exterior surface 38 can be smooth, porous, or define an external thread. As described below, the exterior surface 38 can also define locking features which interface with a fastener or an interior surface of an implant accepting bore to fix the prosthetic assembly 24 within an aperture. Additionally, the exterior surface 38 can be shaped or machined after molding.

Figure 4:
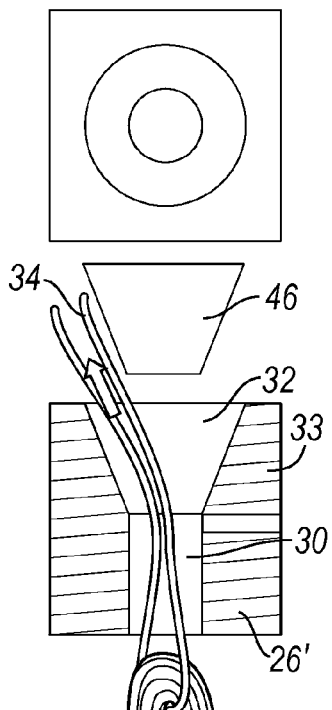
FIG. 4 represents an alternate mold used to form the prosthetics shown in FIGS. 3a-3c.
Figure 6A:
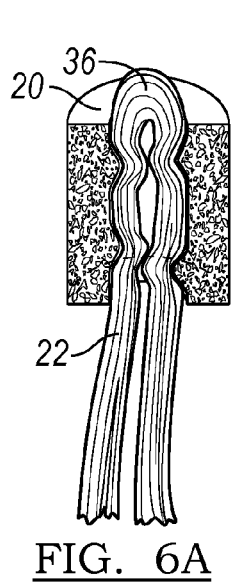
FIGS. 6a-6c represent prosthetics utilizing the tying mechanisms shown in FIGS. 5a-5d.

FIG. 4 represents an alternate mold 33 for forming the prosthetics shown in FIGS. 3a-3c. As shown, the cavity 30 can be defined by a single die 26'. This die 26' defines a generally cylindrical cavity 30, which has a conical injection port 32. The suture 34 can be threaded through the injection port 32, pulling the soft tissue replacement within the cavity 30. After the biocompatible material is placed into the conical injection port 32, a plunger-type cap 46 can be inserted into the conical injection port 32 to press the biocompatible material into the cylindrical cavity. It is envisioned that the injection port 32 can be threaded or configured to be formed to accept a syringe, which can be used to inject biological material or bone cement. The cavity 30 can be tapered to facilitate removal of the prosthetic assembly 24 after setting of the polymer 31. Alternately, the interior surface of the molds 26 can have a plurality of members (not shown) which function to position the graft material 22 centrally within the mold 26. Further, these members can compress the graft material 22 at discrete locations to allow the formation of a plug with interdigitation of cement. (see FIG. 6a).

Figure 6B:
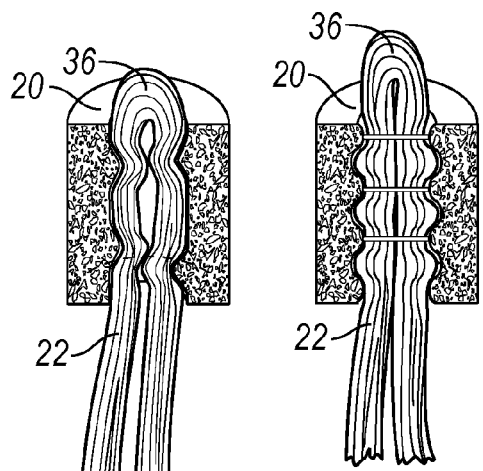
Figure 5A:
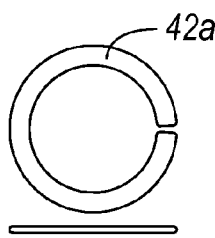
FIGS. 5a-5d represent optional tying mechanisms.
Figure 5B:
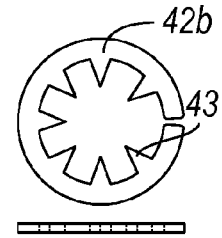
Figure 5C:
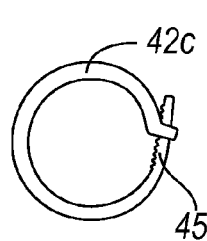
Figure 5D:
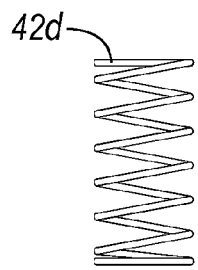

FIGS. 5a-5d represent optional tying mechanisms 42a-42d, which are used to bind the loop 36 of graft material 22. As shown in FIG. 6b, a plurality of tying mechanisms 42a-42d can be annularly disposed about the loop 36 of the graft material 22. The interior surface of the tying mechanisms 42a-42d can be textured 43 so as to prevent the relative displacement of the tying mechanism 42a-42d with respect to the loop 36 of the graft material 22. As shown in FIG. 5c, the tying mechanism 42a-42d can have structures 45 that allow for the non-releasable or releasable tightening of the tying mechanism about the graft loop 36.

Figure 6C:
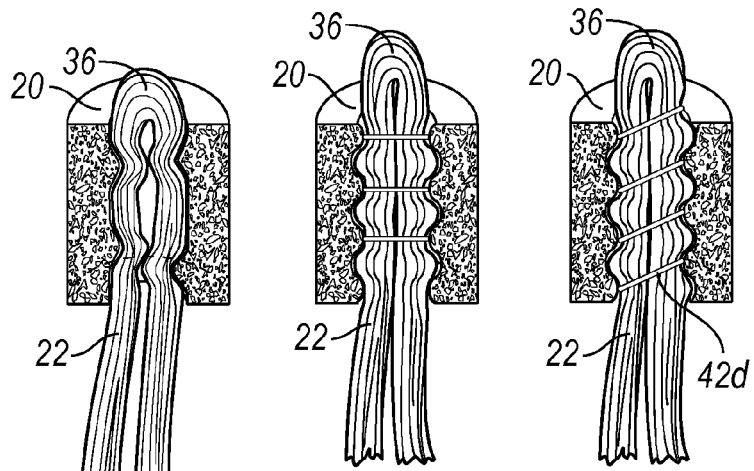

As shown in FIG. 6c, a single tying member 42d can be formed as a coil spring 42d. The coil spring 42d can be radially expanded so as to allow for the insertion of the loop 36 into an inner space defined by the coils of the coil spring 42d. After the tying mechanism is coupled to the graft loop 36, the subassembly is positioned within the mold as disclosed above to form the prosthetic assembly 24. Depicted is a cross-sectional view of the graft loop 36 disposed within the formed prosthetic 20. Shown is the tying mechanism 42d disposed about the graft loop 36 which is fully disposed within the prosthetic 20. While a distal end of the loop 36 of graft material is shown being exposed to allow acceptance of a suture, it is equally envisioned the distal end of the loop 36 can be fully incorporated into the prosthetic 20.

Figure 7A:
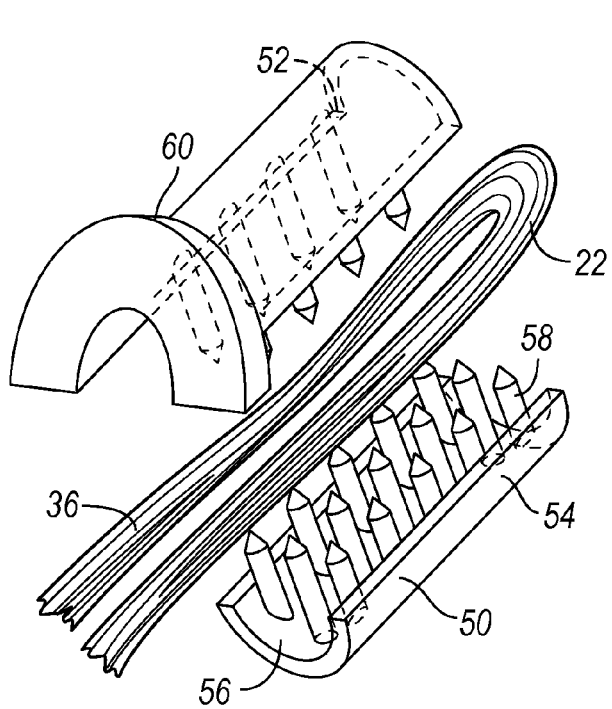
FIGS. 7a and 7b represent coupling an alternate prosthetic to a graft and to the insertion thereof.

FIG. 7a represents an alternate prosthetic 50 configured to be coupled to the loop 36 of the graft material 22. The prosthetic 50, as well as those described below, are formed of first and second members 52 and 54 which are mechanically, ultrasonically, or adhesively coupled together. The members 52 and 54 together define a graft-accepting through-passage 56. Disposed within the through-passage 56 are a plurality of counter-posed graft-engaging members 58. The counter-posed graft-engaging members 58 are configured to pierce or frictionally engage the graft material 22. Additionally, optional coupling surfaces can be formed on the counter-posed graft-engaging members 58 to couple the first and second members 52 and 54 together.

Figure 7B:
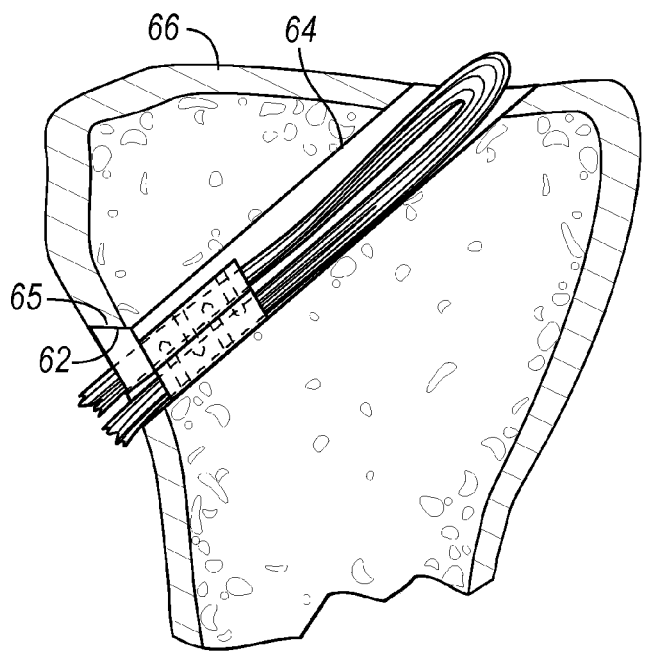

As described above, optionally disposed on an exterior surface of the prosthetic 50 is a bone-engaging bearing surface 60. This bone-engaging bearing surface 60 can be on either or both of the first and second members 52 and 54. FIG. 7b shows the prosthetic 50 disposed within a bore 64 defined in a tibia 66. As shown, the bone-engaging bearing surface 60 has an angled bearing surface 62, which interfaces with a counter sunk surface 65 formed in an outer surface of the tibia 66. The prosthetic 50 is formed of a biocompatible material. In this regard, the material can be any biocompatible material such as metal or polymer such as ultrasonically bondable PEEK, PEKK, or can be a resorbable material such as Lactosorb®.

Figure 8A:
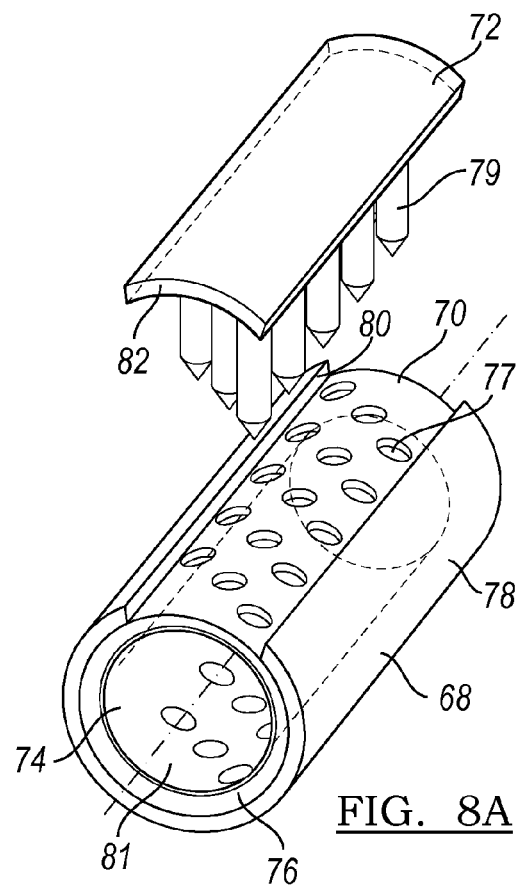
FIGS. 8a and 8b represent an alternate coupling prosthetic.
Figure 8B:
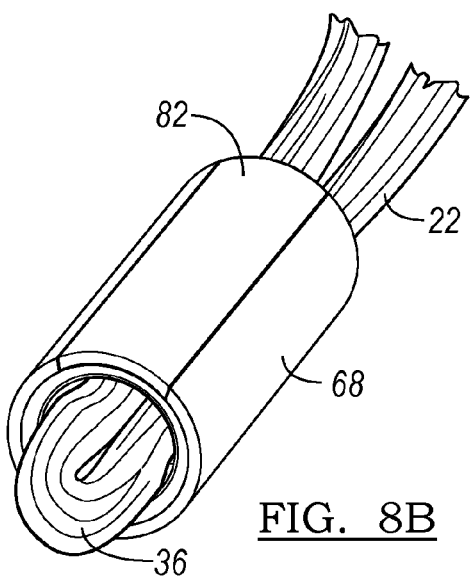

FIGS. 8a and 8b represent perspective views of an alternate prosthetic 68 according to the disclosure herein. The prosthetic 68 is formed of first and second members 70 and 72. The first member 70 is generally cylindrical having a graft loop accepting through-passage 74. The first member 70 can be formed of an inner member 77 and an outer member 78. The inner member 76 defines a plurality of graft-engaging member accepting apertures 77. These apertures 77 can be formed on opposite sides of the first member 70 to facilitate the locking of the graft-engaging second member 72 to the first member 70. The outer member 78 is annularly disposed about the inner member 76. In this regard, the outer member 78 defines a groove 80, which generally surrounds the graft-engaging member apertures 76. The second member 72 is generally arcuate and is configured to be disposed within the groove 80 formed by the outer member 78. Disposed on a convex inner surface 82 of the second member 72 are a plurality of graft-engaging members 79. These graft-engaging members 79 are configured to be aligned with the graft-engaging member apertures 77 formed in the first member 70.

As shown in FIG. 8b, the graft loop 36 is fed through the loop-accepting aperture 81. The graft-engaging members 79 are aligned with the apertures 77. The second member 72 is displaced toward the first member 70, causing the graft-engaging member 79 to pierce or frictionally engage the graft loop 36. The first and second members 70 and 72 are then ultrasonically, adhesively, press-fit or heat bonded together to form a single prosthetic.

As shown in FIGS. 9a-9d, the prosthetic 50 can have a plurality of coupling flanges 84, which can be disposed about a mating surface 86. These flanges 84 are configured to interface with corresponding slots 88 in the first member. As described above, the exterior surface 90 of the implant 50 can be textured. As shown, the exterior surface 90 can define an angled threaded depression 92, which is configured to accept a bone-engaging screw 100 (see FIG. 10). Additionally the exterior surface can define a generally concave threaded depression 93 which runs the length of the length of the implant.

Figure 9A:
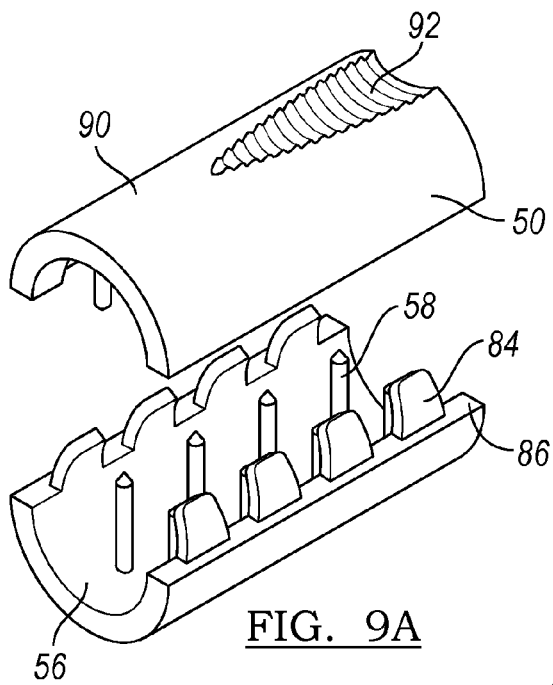
FIGS. 9a-9d represent perspective and side views of an alternate embodiment.
Figure 9B:
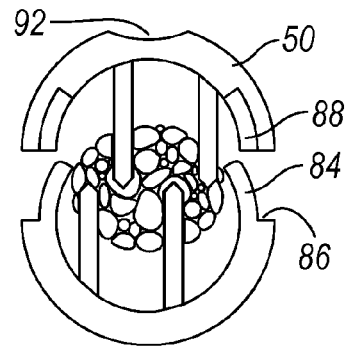
Figure 9C:
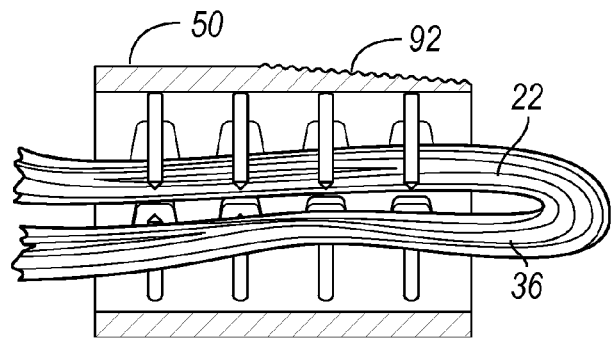
Figure 9D:
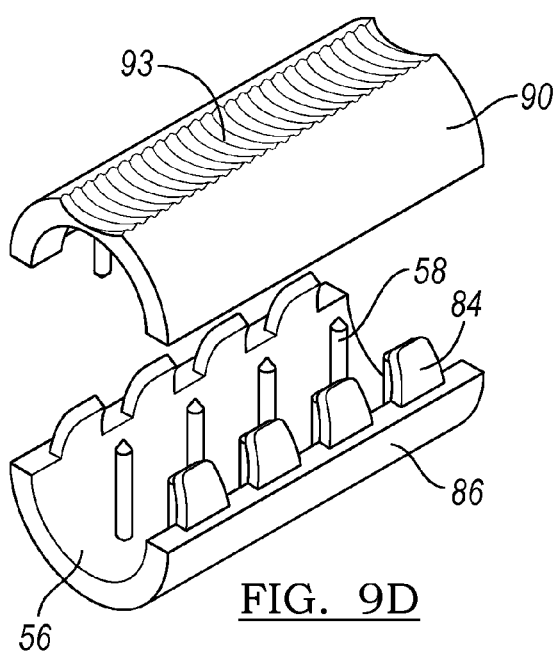
Figure 10:
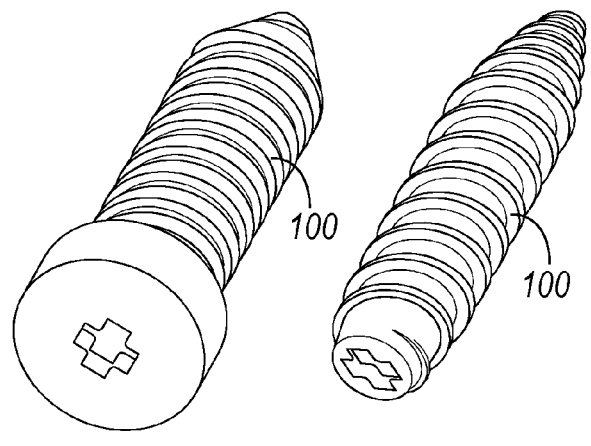
FIG. 10 represents fasteners used to couple the graft construction to a femoral tunnel.
Figure 11:
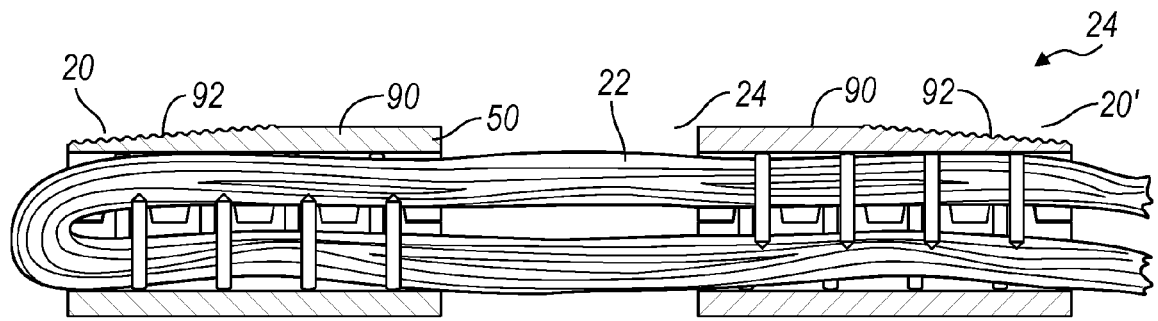
FIG. 11 represents an artificial bone-tendon-bone fastener graft construction.

FIG. 11 represents an artificial bone-tendon-bone prosthetic assembly 24. The assembly 24 includes a pair of prosthetics 20 as shown in FIG. 9d coupled to proximal and distal ends of a loop of graft material. It is envisioned that the prosthetics 20 used to form the artificial bone-tendon-bone prosthetic assembly 24 can utilize any of the aforementioned prosthetics 20. Additionally shown is the suture used to install the artificial bone-tendon-bone prosthetic assembly 24 into the bone.

Figure 12:
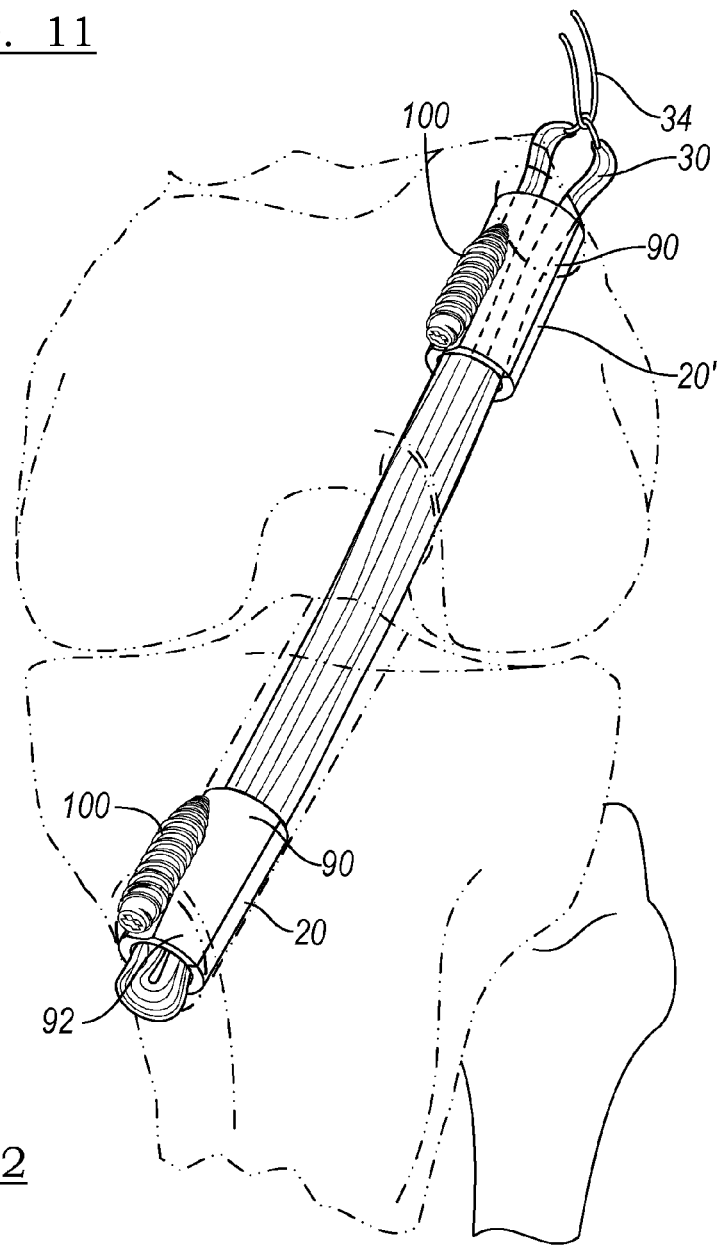
FIG. 12 represents the construction according to FIG. 9c coupled to a tibial and femoral tunnel using the fastener of FIG. 10.

FIG. 12 depicts an implant 50 coupled to a graft 22 disposed within a tibial and femoral tunnel. As mentioned above, the graft 22 is coupled to the prosthetic 20 to form an artificial bone-tendon or bone-tendon-bone prosthetic assembly 24. It is envisioned the physician can intraoperatively determine the desired graft or graft assembly length and appropriate graft tension. The first prosthetic 20 is coupled to a first end of the replacement graft either preoperatively or intraoperatively using any of the methods described above. The physician then determines an appropriate length for the graft material 22 by measuring an anatomical distance.

An appropriate amount of tension is applied to the graft and the length of the graft is then marked. A second prosthetic 20' is then coupled to the prosthetic assembly at the marked location. This location is a function of the measured anatomical distance, which takes into account mounting structures. This provides an appropriately sized artificial bone-tendon-bone prosthetic. It is envisioned the second prosthetic 20 would then be coupled to the graft material intraoperatively. Optionally, a kit of preformed artificial bone-tendon graft assemblies with an associated second prosthetic can be provided. Additionally, the kit can contain the molds 26 or 26' shown in FIG. 1 or 4, and a package of premeasured castable material.

Once the graft assembly 24 is formed, a suture 34 is coupled to the assembly. The suture 34 and prosthetic assembly 24 are threaded into the tunnel formed in the bone or bones, so as to position the prosthetics 20 and 20' near an opening of the tibial and femoral tunnel. A fastener 100 is engagably driven between the implants 50 and the internal surface 94 of the bore 96 formed in the tibia. This locks the graft assembly 24 to the bone. Appropriate tension is applied to the graft, which is fixed at its second end by a soft tissue/bone-engaging fastener 100 or other suitable means.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A device for surgically coupling a soft tissue graft into a tunnel of a bone comprising:
    a first member including a first graft-engaging surface extending from a first end to a second end of the first member, a first bone-engaging surface opposite to the first graft-engaging surface, and a bone-engaging bearing surface that radially extends from the first bone-engaging surface at the first end of the first member in a direction transverse to the longitudinal axis; and
    a second member including a second graft-engaging surface extending from a first end to a second end of the second member, the second member is separate from the first member and configured to couple with the first member to secure the first and the second members together;
    wherein the first graft-engaging surface and the second graft-engaging surface define a graft-accepting through-passage with a longitudinal axis extending therethrough when the first member is secured to the second member;
    wherein the first and the second members are configured to be coupled together such that the bone-engaging bearing surface axially extends beyond the first end of each of the first member and the second member along the longitudinal axis, and such that the first end of the second member is axially offset from the bone-engaging bearing surface along the longitudinal axis;
    wherein the bone-engaging bearing surface is configured to not protrude from an outer surface of the bone when the device is seated in the tunnel;
    wherein the bone-engaging bearing surface is semi-circular and extends from only the first member.

2. The device of claim 1, wherein the first graft-engaging surface and the second graft-engaging surface both include graft-engaging spikes extending into the graft-accepting through-passage.

3. The device of claim 1, wherein the second member includes an inner member and an outer member, the inner member defines a circular through bore, the outer member covers less than an entirety of the inner member and defines a groove between a first edge of the outer member and a second edge of the outer member, a plurality of apertures are defined by the inner member between the first edge and the second edge.

4. The device of claim 3, wherein the first member is configured to fit within the groove and spikes extending from the first member are configured to fit within the apertures.

5. The device of claim 1, wherein the graft-accepting through-passage includes a generally circular cross-section along a line transverse to the longitudinal axis.

6. The device of claim 1, wherein the first member defines a slot configured to couple with a mating surface of the second member.

7. The device of claim 1, wherein the first graft-engaging surface is concave and a first bone-engaging surface opposite to the first graft-engaging surface is convex;
wherein the second graft-engaging surface is concave and a second bone-engaging surface opposite to the second graft-engaging surface is convex; and
wherein the graft-accepting through-passage is generally elongated and tubular shaped.

8. A device for surgically coupling a soft tissue graft into a tunnel of a bone comprising:
a first member including a convex first bone-engaging surface extending from a first end to a second end of the first member, a concave first graft-engaging surface extending from the first end to the second end of the first member that is opposite to the first bone-engaging surface, and a plurality of graft-engaging members included with the first graft-engaging surface; and
a second member including an inner tube and an outer covering, the inner tube has a concave second graft-engaging surface extending from a first end to a second end of the second member, the outer covering has a convex second bone-engaging surface extending from the first end to the second end of the second member opposite to the second graft-engaging surface, the outer covering covers less than an entirety of the inner tube, the outer covering includes a first edge opposing a second edge, a plurality of apertures are defined in the inner tube between the first edge and the second edge, the apertures configured to receive the plurality of graft-engaging members;
wherein the first graft-engaging surface and the second graft-engaging surface define a graft-accepting through-passage when the first member is coupled to the second member; and
wherein the graft-accepting through-passage defines a generally circular cross-section taken along a first line perpendicular to a longitudinal axis extending through the graft-accepting through-passage.

9. The device of claim 8, wherein the first graft-engaging surface includes a plurality of first graft-engaging spikes and the second graft-engaging surface includes a plurality of second graft-engaging spikes.

10. The device of claim 9, wherein the first graft-engaging spikes are offset from the second graft-engaging spikes when the first member and the second member are coupled together.

11. The device of claim 8, wherein a bone-engaging bearing surface extends radially from the first end of the first bone-engaging surface and at least partially along a second line perpendicular to the longitudinal axis, the bone-engaging bearing surface configured to mate with a counter sink formed at an opening of the tunnel of the bone.

12. The device of claim 8, wherein the first member defines a slot and the second member defines a mating surface configured to cooperate with the slot.

13. The device of claim 8, further comprising a fastener; and
wherein the first bone-engaging surface defines a threaded depression configured to cooperate with threads of the fastener.

14. The device of claim 8, wherein the first member and the second member are coupled together one of mechanically, ultrasonically, or adhesively.

15. The device of claim 8, wherein the soft tissue graft is selected from one of a xenograft, an allograft, or an artificial graft material; and
wherein the soft tissue graft is arranged such that a loop portion of the soft tissue graft extends out from a first end of the graft-accepting passage, and two elongated portions of the soft tissue graft extending from the loop portion extend outward from a second end of the graft-accepting passage.

16. A device for surgically coupling a soft tissue graft into a tunnel of a bone comprising:
a first member including a first graft-engaging surface and a first bone-engaging surface, each of which extend from a first end to a second end of the first member, the first bone-engaging surface defines a threaded depression configured to cooperate with threads of a fastener configured to secure the first member at an implant site, the first member defines a slot; and
a second member including a second graft-engaging surface and a second bone-engaging surface, each of which extend from a first end to a second end of the second member, the second member defines a mating surface configured to mate with the slot;
wherein the first graft-engaging surface and the second graft-engaging surface define a graft-accepting through-passage with a longitudinal axis extending therethrough when the first member is secured to the second member;
wherein the second member includes an inner member and an outer member, the inner member defines a circular through bore, the outer member covers less than an entirety of the inner member and defines a groove between a first edge of the outer member and a second edge of the outer member, a plurality of apertures are defined by the inner member between the first edge and the second edge.

17. The device of claim 16, wherein the first member includes a first bone-engaging surface opposite to the first graft-engaging surface, and a bone-engaging bearing surface that radially extends from the first bone-engaging surface and extends in a direction transverse to the longitudinal axis.

18. The device of claim 16, wherein the first grant-engaging surface and the second graft-engaging surface both include graft-engaging spikes extending into the graft-accepting through-passage.

19. The device of claim 16, wherein the graft-accepting through-passage includes a generally circular cross-section along a line transverse to the longitudinal axis.

20. The device of claim 16, wherein the first graft-engaging surface is concave and a first bone-engaging surface opposite to the first graft-engaging surface is convex;
wherein the second graft-engaging surface is concave and a second bone-engaging surface opposite to the second graft-engaging surface is convex; and
wherein the graft-accepting through-passage is generally elongated and tubular shaped.

21. The device of claim 16, wherein the first member is configured to fit within the groove and spikes extending from the first member are configured to fit within the apertures.

22. A device for surgically coupling a soft tissue graft into a tunnel of a bone comprising:

a first member including a first graft-engaging surface extending from a first end to a second end of the first member; and a second member including a second graft-engaging surface extending from a first end to a second end of the second member, the second member is separate from the first member and is configured to couple with the first member to secure the first member and the second member together;

first graft engaging spikes extending from the first graft-engaging surface and terminating prior to reaching the second graft-engaging surface, the first graft engaging spikes are spaced apart along a length of the device, each one of the first graft engaging spikes extend along a maximum length thereof away from the first graft engaging surface; and second graft engaging spikes extending from the second graft-engaging surface and terminating prior to reaching the first graft-engaging surface, the second graft engaging spikes are spaced apart along a length of the device, each one of the second graft engaging spikes extend along a maximum length thereof away from the second graft engaging surface;

wherein the first graft-engaging surface and the second graft-engaging surface define a graft-accepting through-passage with a longitudinal axis extending therethrough when the first member is secured to the second member;

wherein the second member includes an inner member and an outer member, the inner member defines a circular through bore, the outer member covers less than an entirety of the inner member and defines a groove between a first edge of the outer member and a second edge of the outer member, a plurality of apertures are defined by the inner member between the first edge and the second edge; and wherein the first member is configured to fit within the groove and the first spikes extending from the first member are configured to fit within the apertures.

23. The device of claim 22, wherein the first member includes a first bone-engaging surface opposite to the first graft-engaging surface, a bone-engaging bearing surface radially extends from the first bone-engaging surface and extends in a direction transverse to the longitudinal axis.

24. The device of claim 22, wherein the graft-accepting through-passage includes a generally circular cross-section along a line transverse to the longitudinal axis.

25. The device of claim 22, wherein the first graft-engaging surface is concave and a first bone-engaging surface opposite to the first graft-engaging surface is convex;

wherein the second graft-engaging surface is concave and a second bone-engaging surface opposite to the second graft-engaging surface is convex; and wherein the graft-accepting through-passage is generally elongated and tubular shaped.

26. A device for surgically coupling a soft tissue graft into a tunnel of a bone comprising:

a first member including a first graft-engaging surface extending from a first end to a second end of the first member, a first bone-engaging surface opposite to the first graft-engaging surface, and a bone-engaging bearing surface that radially extends from the first bone-engaging surface at the first end of the first member in a direction transverse to the longitudinal axis; and a second member including a second graft-engaging surface extending from a first end to a second end of the second member, the second member is separate from the first member and configured to couple with the first member to secure the first and the second members together;

wherein the first graft-engaging surface and the second graft-engaging surface define a graft-accepting through-passage with a longitudinal axis extending therethrough when the first member is secured to the second member;

wherein the first and the second members are configured to be coupled together such that the bone-engaging bearing surface axially extends beyond the first end of each of the first member and the second member along the longitudinal axis, and such that the first end of the second member is axially offset from the bone-engaging bearing surface along the longitudinal axis;

wherein the bone-engaging bearing surface is configured to not protrude from an outer surface of the bone when the device is seated in the tunnel; and wherein the bone-engaging bearing surface is configured to be seated in a counter-sunk surface formed in an outer surface of the bone.

27. A device for surgically coupling a soft tissue graft into a tunnel of a bone comprising:

a first member including a first graft-engaging surface extending from a first end to a second end of the first member, a first bone-engaging surface opposite to the first graft-engaging surface, and a bone-engaging bearing surface that radially extends from the first bone-engaging surface at the first end of the first member in a direction transverse to the longitudinal axis; and a second member including a second graft-engaging surface extending from a first end to a second end of the second member, the second member is separate from the first member and configured to couple with the first member to secure the first and the second members together;

wherein the first graft-engaging surface and the second graft-engaging surface define a graft-accepting through-passage with a longitudinal axis extending therethrough when the first member is secured to the second member;

wherein the first and the second members are configured to be coupled together such that the bone-engaging bearing surface axially extends beyond the first end of each of the first member and the second member along the longitudinal axis, and such that the first end of the second member is axially offset from the bone-engaging bearing surface along the longitudinal axis;

wherein the bone-engaging bearing surface is configured to not protrude from an outer surface of the bone when the device is seated in the tunnel; and wherein the bone-engaging bearing surface includes a side surface extending at a non-parallel and non-orthogonal angle relative to the longitudinal axis.

* * * * *

UNITED STATES PATENT AND TRADEMARK OFFICE
CERTIFICATE OF CORRECTION

| | | |
|---|---|---|
| PATENT NO. | : 8,900,301 B2 | Page 1 of 1 |
| APPLICATION NO. | : 13/419681 | |
| DATED | : December 2, 2014 | |
| INVENTOR(S) | : Kevin T. Stone et al. | |

It is certified that error appears in the above-identified patent and that said Letters Patent is hereby corrected as shown below:

In the specification,

Column 5, Line 9; Delete "77" and insert --76--.

Column 5, Line 17; Delete "76" and insert --77--.

Signed and Sealed this
Twenty-eighth Day of April, 2015

Michelle K. Lee
*Director of the United States Patent and Trademark Office*